Figure 1:
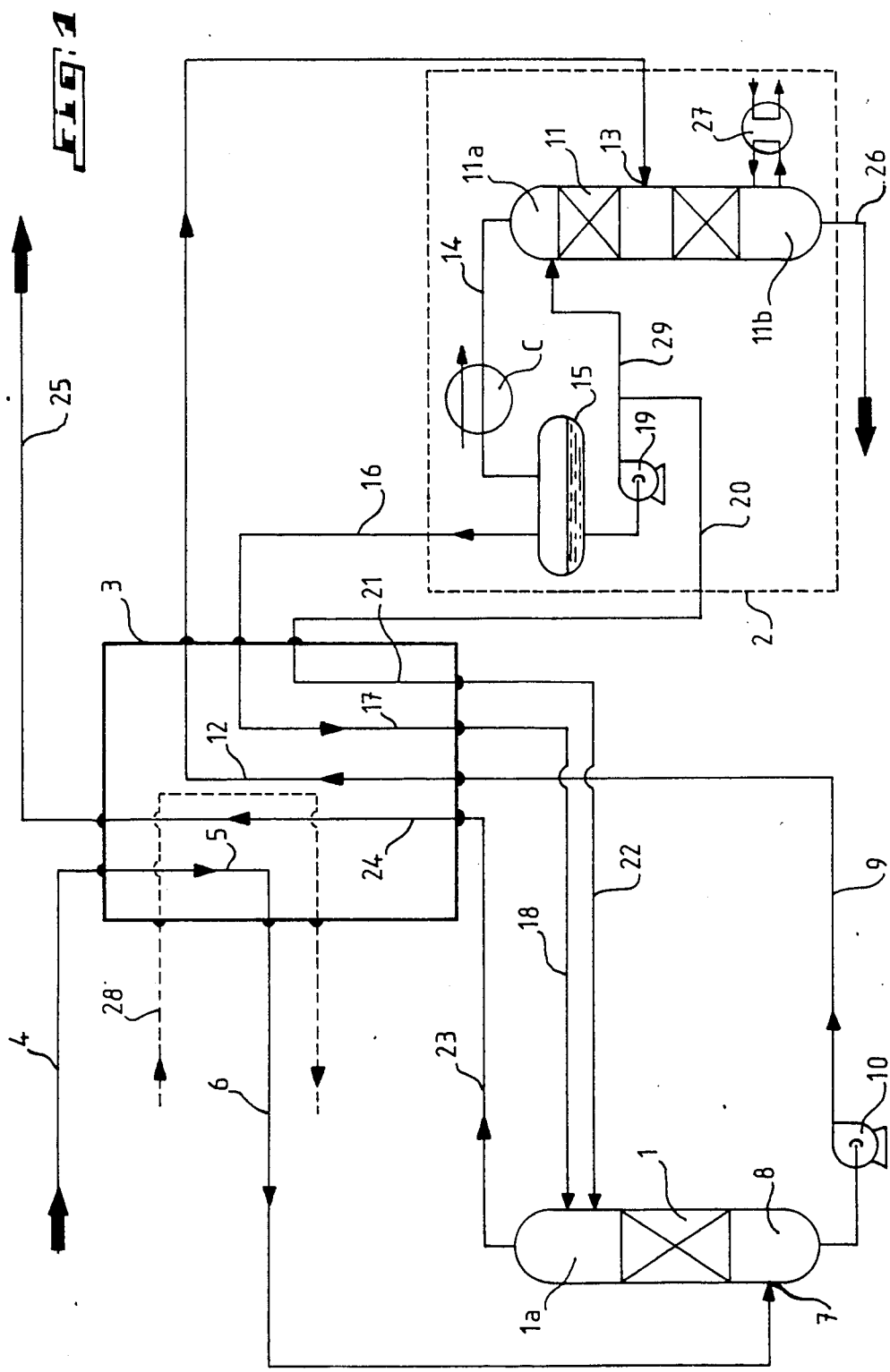

United States Patent [19]

Paradowski et al.

[11] Patent Number: 4,690,702

[45] Date of Patent: Sep. 1, 1987

[54] METHOD AND APPARATUS FOR CRYOGENIC FRACTIONATION OF A GASEOUS FEED

[75] Inventors: Henri Paradowski, Cergy-Pontoise; Joëlle H. Castel, Le Pont Marly; Hervë B. Parfait, Paris, all of France

[73] Assignee: Compagnie Francaise d'Etudes et de Construction "Technip", Paris, France

[21] Appl. No.: 779,811

[22] Filed: Sep. 25, 1985

[30] Foreign Application Priority Data

Sep. 28, 1984 [FR] France .................................. 84 14996

[51] Int. Cl.$^4$ ................................................. F23J 3/06
[52] U.S. Cl. ........................................... 62/23; 62/38
[58] Field of Search .................. 62/27, 28, 23, 24, 38; 55/48

[56] References Cited

U.S. PATENT DOCUMENTS

| | | | |
|---|---|---|---|
| 2,952,984 | 9/1960 | Marshall, Jr. | 62/27 |
| 3,436,925 | 4/1969 | Jakob | 62/27 |
| 4,251,249 | 2/1981 | Gulsby | 62/28 |
| 4,273,566 | 6/1981 | Schwarz | 62/27 |
| 4,322,225 | 3/1982 | Bellinger et al. | 55/27 |
| 4,444,576 | 4/1984 | Ryan et al. | 62/28 |
| 4,526,595 | 7/1985 | McNeil | 62/28 |

FOREIGN PATENT DOCUMENTS 449816 1/1973 Australia.

OTHER PUBLICATIONS

French Search Report FR 84 14996 (and translation).

*Primary Examiner*—Ronald C. Capossela
*Attorney, Agent, or Firm*—Kenyon & Kenyon

[57] ABSTRACT

The invention relates to a method and an apparatus for cryogenic fractionation of a gaseous feed comprising a contact purifying-refrigerating column into the bottom of which is injected a partially condensed gaseous feed, the said column producing in its head portion a residual gas and in its bottom portion a liquid which is injected into a fractionating column producing in its head portion a distillate which is at least partially condensed and injected into the head portion of the column to thus recover in the bottom liquid of this column the heavy compounds contained in the vaporized fraction of the gaseous feed.

16 Claims, 3 Drawing Figures

METHOD AND APPARATUS FOR CRYOGENIC FRACTIONATION OF A GASEOUS FEED

The present invention has essentially for a subject matter a method of cryogenic fractionation of any gaseous feed such as for example natural gas, gases associated with hydrocarbon condensates, or gases resulting from the processing of petroleum fractions.

It is also directed to an apparatus for carrying out the said method.

There have already been proposed many industrial apparatuses for the fractionation of a gaseous feed into a residual gas containing the more volatile compounds of the gaseous feed and into a liquid product containing the heaviest compounds thereof, with a view to obtaining in the said liquid product a desired constituent of the gaseous feed with a high recovery ratio.

In this respect, mention may be made for example of the recovery of liquefied petroleum gas ($C_3$ to $C_4$ hydrocarbons) from natural or refinery gas, the recovery of ethane intended particularly to be supplied to vapor-cracking units, or the desulfuration of or gasoline removal from natural gas through recovery of sulfur-containing compounds such as carbon oxysulfide and mercaptans.

Generally, in all such known apparatuses, the gaseous feed is partially condensed by being cooled to a low temperature and is thereafter separated in a separator. Thereafter, the liquid portion is processed in a conventional fractionating column, and there are recovered, in the bottom of this column, in liquid form, the desired heavy compound or compounds of the gaseous feed. In some cases, a refrigeration cycle is provided to meet the needs of the plant for cold.

However, apparatuses of this kind suffer from disadvantages because, if it is desired to obtain in the bottom of the fractionating column a particular heavy compound with a high recovery ratio, a large portion of the light compounds must be condensed upstream of the fractionating column, and this understandably requires a low temperature during the refrigeration of the gaseous feed as well as in the fractionating column head system.

In other words, in the known apparatuses using a simple separator, it is necessary to condense many light compounds in order to condense all the heavy compounds, which requires the supply of a considerable amount of cold, so that such apparatuses consume much energy owing to the power required to produce the cold.

The invention therefore has mainly for a purpose to solve this major problem by providing a method and an apparatus allowing the amount of light compounds introduced into the fractionating column to be reduced to a minimum, so as to substantially reduce the consumption of energy by the apparatus and more particularly the power consumed for supplying the cold.

To this end, the invention has for a subject matter a method of cryogenic fractionation of any gaseous feed into a residual gas containing the most volatile compounds of the feed and into a liquid product containing the heaviest compounds of the said feed, characterized in that the said feed partially condensed is injected into the bottom of a contact purifying-refrigerating column, which column produces at its head all or part of the residual gas, and at its bottom, a liquid which is injected into a fractionating column to obtain in the bottom of the latter a liquid product containing the heaviest compounds of the gaseous feed, and at its head, a distillate which is at least partially condensed and injected as head supply to the said purifying-refrigerating column to thus recover in the liquid at the bottom of this column a heavy compound present in the vaporized fraction of the gaseous feed.

It is therefore already understood that the provision of a contact purifying-refrigerating column instead of a simple separator on the partially condensed gaseous feed advantageously allows recovering the desired compound at the bottom of this column owing to the essentially liquid supply injected into its head portion and which ensures the cooling and selective condensation of the heavy compounds of the gaseous fraction with minimum condensation of the lighter compounds. Therefore, the cooling temperatures of the feed and at the head of the fractionating column are higher and thus the consumption of energy for producing the cold is markedly reduced.

According to another feature of the method of the invention, the head supply to the said purifying-refrigerating column is constituted by the vapor distillate of the fractionating column, partially or wholly condensed in an exchange system, and/or by the liquid distillate from the said fractionating column, either subcooled or not subcooled in the said system.

The said method is also characterized by the fact that the said fractionating column operates at a higher pressure than that of the contact purifying-refrigerating column to allow the injection of the distillate from the fractionating column into the purifying-refrigerating column without compression of the said distillate.

According to a further feature of the method, a complementary amount of cold at a low temperature level, necessary for the cooling of the gaseous feed to a low temperature and for its partial condensation prior to its injection into the purifying-refrigerating column, necessary for the cooling of the distillate or distillates of the fractionating column, and also necessary to the condensation system of the latter, is supplied by a refrigeration system.

According to one form of embodiment, the refrigeration system is constituted by a compression refrigeration cycle in which a refrigerating fluid including one or several pure substances is brought to a high pressure in a compressor and then condensed and, if suitable, subcooled at that pressure and lastly expanded to the pressure or pressures compatible with the temperature levels of the exchange systems of the process in order to be vaporized in the said systems.

According to another form of embodiment, the refrigeration system is constituted by the expansion of the residual gas leaving the purifying-refrigerating column, in order to lower its temperature to a level compatible with the temperatures of the exchange systems of the process, the said expansion being, if suitable, associated with the aforesaid refrigeration cycle.

According to still another form of embodiment, the said refrigeration system is constituted by the expansion of the gaseous feed in a turbine-expander ensuring a partial condensation of the said feed and producing mechanical energy which is used to drive a rotary machine, and a complementary amount of cold is supplied, if suitable, by the said refrigeration cycle.

Use may of course be made, without departing from the scope of the invention, of any other expansion means allowing a partial condensation of the gaseous feed and performing or not performing external work.

The invention is also directed to an apparatus for carrying out the above method, the said apparatus being essentially characterized by the association of a contact purifying-refrigerating column with a fractionating column.

The apparatus of the invention is also characterized by a distillate supply conduit connecting the fractionating column head to the purifying-refrigerating column head after passing through an exchange system upstream of the latter, and by a conduit connecting the purifying-refrigerating column bottom to the fractionating column after passing through the said exchange system.

It is to be noted that at least one gaseous feed intake conduit is connected to the bottom of the purifying-refrigerating column and a residual gas discharge conduit is connected to the head of the said column, these two conduits passing through the said exchange system.

According to another feature of the apparatus of the invention, there are provided at the head of the fractionating column a condenser and reflux drum provided, on the one hand, with a first, gaseous-distillate supply conduit passing through the said exchange system and leading into the purifying-refrigerating column head, and on the other hand, with a second, liquid distillate reflux conduit leading into the fractionating column head, the said second conduit being, if suitable, connected to the purifying-refrigerating column head by a conduit passing through the said exchange system to supply the said column with subcooled liquid distillate.

The apparatus of the invention is also characterized in that a refrigerating fluid circuit is associated, if suitable, with the said exchange system.

According to another form of embodiment, there is provided at the head of the fractionating column a condenser to which cold is supplied by a refrigerating fluid circuit associated with the said exchange system.

According to still another form of embodiment of the apparatus of the invention, the fractionating column head is provided with a vapor distillate conduit passing through the said exchange system and leading into a liquid distillate reflux drum connected to the said column, which reflux drum is provided with a gaseous distillate supply conduit passing through the said exchange system and leading into the purifying and refrigerating column head.

It is to be noted that the gaseous-feed intake conduit, after passing through the exchange system, is connected to a separator whose bottom is provided with a liquid fraction outflow path leading into the bottom of the purifying-refrigerating column and whose head is provided with a gaseous fraction passage path leading to the inlet of a turbine-expander whose outlet is connected to the bottom of the said column.

According to still another feature of the above variant of embodiment of the plant, the said turbine expander drives at least one rotary machine such as, for example, a compressor connected to the residual gas discharge conduit.

Figure 2:
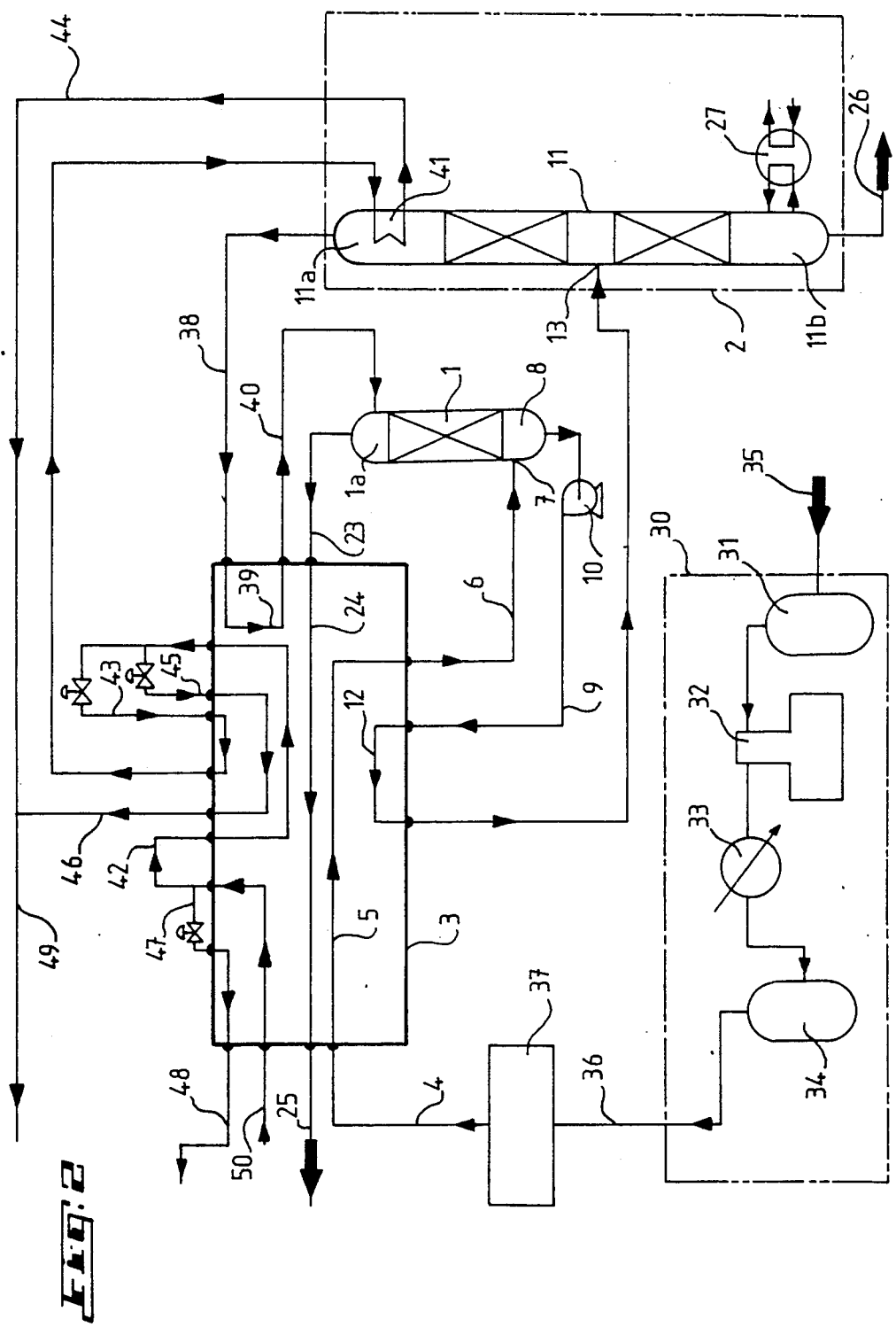
Figure 3:
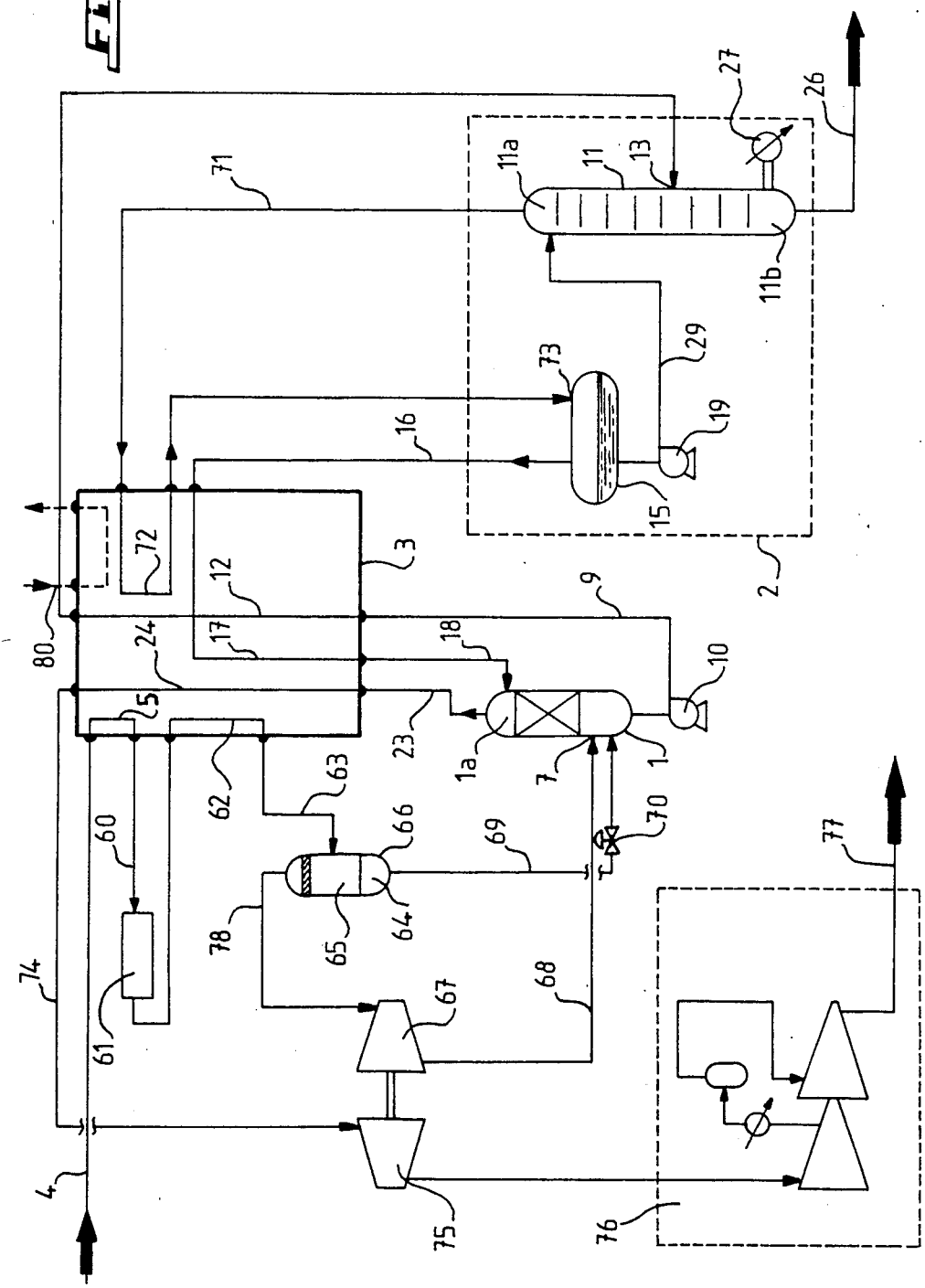

Other features and advantages of the invention will appear more clearly as the following detailed description proceeds with reference to the appended drawings given solely by way of example and wherein:

FIG. 1 is a diagrammatic view of a gaseous-feed fractionating apparatus according to the principles of the invention;

FIG. 2 diagrammatically illustrates one example of embodiment of an apparatus according to the invention using a system for direct refrigeration by means of a refrigeration cycle in order to recover the $C_3^+$ hydrocarbon compounds from refinery gas; and FIG. 3 diagrammatically illustrates another example of embodiment of an apparatus according to the invention allowing the recovery of gasoline from natural gas.

Reference is first made to FIG. 1 which illustrates the principle of an apparatus according to the invention, the structure and operation of which is described hereafter.

The apparatus includes essentially a contact purifying-refrigerating column 1, a fractionating column assembly 2 and an exchange system 3.

The gaseous feed to be processed, consisting of a mixture of heavy and light compounds, is flowed to the apparatus through a conduit 4 after having been subjected to a compression stage (not shown). The conduit 4 follows the conduit portion 5 passing through the exchange system 3 where the said gaseous phase is cooled to provide a partially condensed fluid which is injected at 7, through the conduit portion 6, into the bottom of the purifying-refrigerating column 1. The liquid 8 contained in the bottom of this column and including heavy compounds together with a minimum quantity of light compounds is flowed through a conduit 9 equipped with a pump 10 to a fractionating column 11 forming part of the fractionating assembly 2. More precisely, the conduit 9 follows a conduit portion 12 in which the liquid portion 8 is heated before being injected at 13 into the fractionating column 11.

At the head of the column 11 is provided an external refrigerant condenser C mounted on a conduit 14 connecting the head 11a of the column 11 to a reflux drum 15. The condenser C ensures an at least partial condensation of the gaseous fraction proceeding from the head of the column 11 and containing a minimum quantity of light compounds.

The reflux drum 15 is provided with a first conduit 16 for the supply of gaseous distillate which is cooled in the exchange system 3 by passing through the conduit portion 17 to be condensed at least partially and thus injected through the conduit portion 18 into the head portion 1a of the purifying-refrigerating column.

The reflux drum 15 is provided with a second conduit 29 equipped with a pump 19 for flowing the reflux into the head 11a of the column 11.

According to a preferred form of embodiment, the liquid distillate may be injected into the head portion 1a of the column 1 through conduits 20, 21 and 22 connecting the reflux conduit 29 to the head portion 1a, as is clearly seen in the Figure. More precisely, the conduit 20 includes a portion 21 passing through the exchange system 3 where the liquid distillate is subcooled before flowing through the conduit 22 into the head portion 1a of the purifying-refrigerating column 1.

The residual gas leaving the head 1a of this column through a conduit 23 is heated in an exchange system 3 by passing through the conduit portion 24 before leaving the apparatus through the conduit 25.

Of course, a liquid product including the heavy compound or compounds is collected from the bottom 11b of the fractionating column 11 through a discharge conduit 26. A reboiler 27 is connected to the bottom 11b of the fractionating column 11.

Lastly, there is diagrammatically shown at 28 a refrigerating fluid circuit associated with the exchange system 3 and which, if suitable, may be provided to supply the plant with the complementary amount of cold needed.

The operation of the apparatus is readily inferred from the foregoing description, but stress will be laid here on the role of the purifying-refrigerating column 1, which is essential.

Indeed, owing to the wholly or partially liquid supplies 18 and 22 injected into the head of the column 1, the heavy compounds of the fraction vaporized in this column are condensed and recovered in the bottom of the latter with a minimum condensation of the light compounds, the residual gas 23 flowing out from the head 1a of the said column being very cold and colder than the liquid supplies 18 and 22.

As a result, compared to the conventional apparatuses using a simple separator, the plant of the invention provides many advantages consisting particularly in that the gaseous-feed cooling temperatures and the temperatures in the fractionating column head condenser may be very high, and in that the feed to the fractionating column and the thermal load on its head condenser are reduced.

Under such conditions, the amount of energy consumed by such an apparatus is substantially reduced, as also the cost of the exchange and compression equipment.

The advantages of the invention will be further illustrated by the following description of two forms of embodiment given solely as non-limitative examples of the many applications of which the present invention is capable.

Reference is first made to FIG. 2 which shows an apparatus designed according to the invention in association with a system for direct refrigeration by means of a refrigeration cycle for the recovery of the $C_3+$ cut from a gaseous feed constituted by refinery gas at low pressure (5 bars) of the following composition:

| Constituents | per cent by volume |
|---|---|
| Hydrogen | 12 |
| Nitrogen | 4 |
| $CO_2$ | 2 |
| Methane | 37 |
| C2 cut | 23 |
| C3 cut | 18 |
| C4+ cut | 4 |

It will be noted that the ratio of recovery of the $C_3+$ desired is 99%.

In FIG. 2, the same reference numerals are used as those of FIG. 1 to designate the common elements, namely, the essential elements of an apparatus designed according to the principles of the invention.

As seen in FIG. 2, the gaseous feed to be processed is first flowed into a compression section 30 including a suction drum 31, a compressor 32, a gas cooler 33 and a separating drum 34. In this compression section 30, the fluid gas 35 is compressed to a pressure of 6.2 bars and the gas thus compressed is flowed through a conduit 36 to a desiccating section 37 which, as known per se, provides a desiccated gas which, as described in connection with FIG. 1, is injected at 7 into the bottom of the purifying-refrigerating column 1 after flowing through the conduit 4, the conduit 5 passing through the exchange system 3, and the conduit 6. The gas is thus cooled to a temperature of about $-62°$ C. and the fluid leaving the exchange system 3 through the conduit 6 connected to the column 1 is at a pressure of 5.1 bars.

At 38 is shown a conduit through which flows the distillate leaving the fractionating column 11 and which is almost wholly condensed after passing at 39 through the exchange system 3 and before being finally injected through the conduit 40 into the head 1a of the purifying-refrigerating column. The fluid in the conduit 40 is at a temperature of about $-62°$ C.

The gas at 5 bars leaving the column 1 at 23 is heated to 29° C. in the exchange system 3 to provide, as described in connection with FIG. 1, a residual gas which is flowed out of the apparatus through the conduit 25.

The liquid 8 flowing out from the bottom of column 1 is pumped at 6.6 bars into the pump 10 and is thereafter heated to $-25°$ C. in the exchange system 3 (conduit 12) to provide a flow which is injected at 13 into the fractionating column 11 which is equipped at its bottom with a reboiler 27, and in its head portion 11a, with an incorporated condenser 41. The fractionating column 11 operates at a pressure of 6.3 bars and produces at its top 11a the aforementioned vapor distillate which leaves the column through the conduit 38, and at its bottom, the liquid $C_3+$ cut which is flowed out of the apparatus through the conduit 26.

At the condenser 41, the cold is supplied through a refrigerating fluid circuit associated with the exchange system 3 and which will be described hereafter.

The cold is supplied to the condenser 41 by a portion of the refrigerating fluid 42 expanded at low pressure at 43 and vaporized at 44 after passing through 41. The remainder of the liquid refrigerating fluid 42 is expanded at low pressure at 45 and then vaporized in the exchange system 3 at 46 to thus provide the low-temperature cold necessary to the exchange system 3.

A portion 47 of the liquid refrigerating fluid is vaporized at medium pressure in the exchange system to provide a flow 48, thus allowing the supply of medium-temperature cold necessary to the process.

The vapor refrigerating fluid 49 at low pressure, which is a mixture of the fluids 44 and 46 is flowed back to the low-pressure stage of the compressor (not shown) of the refrigeration cycle.

The vapor refrigerating fluid 48 at medium pressure is flowed back to the medium pressure stage of the said compressor.

Lastly, at the discharge of this compressor, the refrigerating fluid is condensed in a conventional exchanger (not shown) and then flowed back to the apparatus to be re-utilized at 50.

Applicant has found that, in the above-described apparatus, the power consumed by the refrigeration cycle is reduced by 20 per cent compared to the conventional apparatuses, i.e. to the apparatuses using a simple separator drum but not a contact purifying-refrigerating column.

Reference is now made to FIG. 3 which illustrates a unit for the recovery of gasoline from natural gas having the following composition:

| Constituents | Mole per cent |
|---|---|
| Nitrogen | 0.5 |
| $CO_2$ | 3.1 |
| Methane | 65.5 |
| Ethane | 13.4 |
| Propane | 9.4 |
| Butanes | 5.1 |

| Constituents | Mole per cent |
|---|---|
| Pentanes | 2 |
| Hexane and heavier constituents. | 1 |

This unit allows recovering liquefied petroleum gases (C3/C4 cut) with a C4 recovery ratio which is higher than 95% and with a C3/C4 ratio in the said cut equal to 30/70 by volume.

In FIG. 3, the same reference numerals have been used as in FIG. 1 to designate the common elements.

The gaseous feed which is available at a low pressure (5 bars) is compressed in a compression section (not shown) up to 49 bars and then flowed to the apparatus through the conduit 4.

The gaseous flow thereafter flows through the conduit 5 and is thus cooled to 20° C. in the exchange system 3. Thereafter, it is flowed through a conduit 60 into a dessiccating section 61 known per se.

The dessiccated gas is thereafter cooled at 62 to about 13° C. by passing through the exchange system 3 to provide a flow 63 which, at this stage, is partially condensed.

The liquid and vapor phases 64 and 65, respectively, are separated in a separator 66.

The vapor phase 65 is flowed through a conduit 78 to the inlet of a turbine expander 67, so that, at the outlet of the latter, the said vapor phase is expanded to a pressure of about 16 bars and the flow 68 is supplied at 7 into the bottom of the purifying-refrigerating column 1.

The liquid phase 64 from the separator 66 is also supplied into the bottom of the column 1 through a conduit 69 equipped with an expansion valve 70.

The vapor distillate leaving the fractionating column assembly 2 flows through the conduit 16, is condensed at 17 in the exchange system 3 and is injected through the conduit 18 into the head portion 1a of the column 1 as already described in connection with FIG. 1. It is to be noted that this vapor distillate is condensed in the exchange system 3 by the cold residual gas 23 proceeding from the column 1 and by the liquid stream flowing from the bottom of the said column 1 through the conduit 9.

This flow is heated to about 40° C. and then injected at 13 into the fractionating column 11 which produces in its bottom 11b the C3+ cut collected at 26, and at its top, a vapor distillate which flows out through a conduit 71. This distillate is cooled and condensed at 72 in the exchange system 3 and then injected at 73 into the reflux drum 15 already described in connection with FIG. 1. Therefore, there are again seen in this arrangement the conduit 29 for a liquid distillate reflux and the conduit 16 for the supply of the distillate to the purifying-refrigerating column 1 after at least partial condensation in the exchange system 3.

The cold necessary to the condensation system of the fractionating column 11 is supplied to the exchange section 3 through a refrigerating fluid (i.e. propane) circuit 80.

The residual gas produced at 23 and leaving the column 1 is heated to about 40° C. in the exchange system 3 and is then flowed through the conduit portion 74 to a compressor 75 coupled to a turbine expander 67. Lastly, the gas compressed at 75 is flowed to a compression section 76 which does not need to be described in detail here and which allows the residual gas to be delivered at 77 at a high pressure of about 82 bars.

It has been found that, compared to a conventional apparatus including a simple separating drum, the application of the invention in an apparatus such as shown in FIG. 3 offers many advantages.

It allows in particular to improve the butane extraction ratio from 95% in the apparatus including a separating drum to 99% in the apparatus of FIG. 3, without modifying the gaseous-feed and produced-gas compressors.

Moreover, it allows a substantial simplification of a propane refrigeration cycle which includes only one compression stage (whereas in the conventional apparatus two such stages were necessary), owing to a better adjustment of the temperature levels and to the reduction in the thermal load of the condenser and in the cooling of the feed. This results in a power saving of the order of 10% as well as a reduction in equipment costs.

These advantages appear from the following table:

|  | Conventional arrangement | Arrangement according to the invention |
|---|---|---|
| Butane extraction ratio | 95% | 99% |
| Energy consumption |  |  |
| Feed compressor | 11 MW | 11 MW |
| Produced gas compressor | 6.6 MW | 6.6 MW |
| Refrigeration cycle | 1.6 MW | 0.2 MW |
| TOTAL | 19.2 MW | 17.8 MW |

The present invention therefore allows obtaining apparatuses which, with a same gaseous feed flow rate and a same ratio of recovery of one or several compounds of the feed in the liquid product in the bottom of the fractionating column, enable the energy consumption to be reduced by 10 to 40 per cent with respect to the conventional apparatuses using the same refrigeration technique but in which no contact purifying-refrigerating column associated with a fractionating column is used.

Of course, the invention is by no means limited to the forms of embodiment described and illustrated which have been given by way of example only.

On the contrary, the invention includes all technical equivalents to the means described as well as their combinations if the latter are carried out according to its gist.

What is claimed is:

1. A method of cryogenic fractionation of a gaseous feed into a residual gas containing the most volatile compounds of the feed and into a liquid product containing the heaviest compounds of the feed, comprising the steps of:
   injecting said feed in a partially condensed state into the bottom portion of a contact purifying-refrigerating column, which column produces in its head portion at least some of said residual gas, and in its bottom portion, a liquid;
   withdrawing said liquid from said contact purifying-refrigerating column and injecting said liquid into a fractionating column to obtain in the bottom portion thereof a liquid product containing the heaviest compounds of the feed, and in the head portion thereof, a distillate;
   withdrawing said distillate from said fractionation column, and partially condensing and injecting said distillate as head supply into the said purifying-refrigerating column and recovering from the bottom of the fractionating column a liquid containing the heavy compounds contained in the vaporized fraction of a gaseous feed.

2. A method according to claim 1 wherein the head supply to the said purifying-refrigerating column is constituted by the vapor distillate from the fractionating column, either partially or wholly condensed in an exchange system, and/or by the liquid distillate from the said fractionating column, either subcooled or not subcolled in the said exchange system.

3. A method according to claim 1 wherein the said fractionating column operates at a higher pressure than that of the contact purifying-refrigerating column to allow the injection of the distillate from the fractionating column into the purifying-refrigerating column without compression of the said distillate.

4. A method according to claim 1, wherein a complimentary amount of cold at a low temperature level, necessary for the cooling of the gaseous feed to a low temperature and for its partial condensation prior to injection into the purifying-refrigerating column, necessary for the cooling of the fractionating column distillate or distillates, and necessary also to the condensation system of this column, is supplied by a refrigeration system.

5. A method according to claim 4, wherein the refrigeration system is constituted by a compression refrigeration cycle in which a refrigerating fluid including one or several pure substances is compressed to a high pressure in a compressor and then condensed and subcooled at the said pressure and lastly expanded to a pressure or to pressures compatible with the temperature levels of the exchange systems of the process in order to be vaporized in the said systems.

6. A method according to claim 4, wherein the said refrigeration system is constituted by the expansion of the residual gas leaving the purifying-refrigerating column in order to lower its temperature to a level compatible with the temperatures of the exchange systems of the process, the said expansion being, if suitable, associated with the said refrigeration cycle.

7. A method according to claim 4, wherein the said refrigeration system is constituted by the expansion of the gaseous feed in a turbine expander ensuring a partial condensation of the said feed and producing mechanical energy which is used to drive a rotary machine, a complementary amount of cold being provided by the said refrigeration cycle.

8. An apparatus for cryogenic fractionation of a gaseous feed, comprising a contact purifying-refrigeration column having a head and bottom; a fractionating column; means for transferring liquid from the bottom of said contact purifying-refrigerating column to said fractionating column, and means to transfer distillate from said fractionating column to the head of said contact purifying-refrigerating column.

9. An apparatus according to claim 8, wherein at least one distillate supply conduit 16, 18; 38, 40 connecting the head portion of the fractionating column 2, 11 to the head portion of the purifying-refrigerating column 1 after passing (17, 39) through an exchange system 3 upstream of the latter, and by a conduit 9 connecting the bottom portion of the purifying-refrigerating column to the fractionating column after passing (12) through the said exchange system.

10. An apparatus according to claim 9, wherein the said exchange system 3 is associated, with a refrigerating fluid circuit 28.

11. An apparatus according to claim 9, wherein the head portion 11a of the fractionating column 11 proper is equipped with a condenser 41 to which cold is supplied through a refrigerating fluid circuit associated with the said exchange system.

12. An apparatus according to claim 9, wherein the head portion 11a of the said fractionating column is provided with a vapor distillate conduit 71 passing through the said exchange system and leading into a liquid-distillate reflux drum 15 connected to said column, which reflux drum is provided with a gaseous-distillate supply conduit 16, 17, 18 passing through the said exchange system and leading into the head portion 1a of the purifying-refrigerating column 1.

13. An apparatus according to claim 12, wherein the gaseous-feed intake conduit 4 which, after passing (5, 62) through the exchange system 3, leads into a separator 66 provided at its bottom with a liquid fraction outflow path 69 leading into the the bottom portion of the purifying-refrigerating column 1, and provided at its top with a gaseous-fraction passageway 78 leading to the inlet of a turbine expander 67 whose outlet is connected (68) to the bottom portion of the said column 1.

14. An apparatus according to claim 13, wherein the said turbine expander 67 drives at least one rotary machine, such as a compressor 75, connected to the residual gas discharge conduit 74.

15. An apparatus according to claim 8, wherein at least one gaseous-feed intake conduit 4 connected to the bottom portion of the purifying-refrigerating column 1 and by a residual gas discharge conduit 23 connected to the head portion 1a of the said column, both of these conduits passing through the said exchange system 3.

16. An apparatus according to claim 8, wherein in that the head portion of the said fractionating column is provided with a condenser C and a reflux drum 15 provided, on the one hand, with a first, gaseous-distillate supply conduit 16, 17, 18 passing through the exchange system 3 and leading into the head portion 1a of the purifying-refrigerating column 1, and on the other hand, with a second, liquid reflux conduit 29 leading into the head portion 11a of the fractionating column proper, the said second conduit being connected to the head portion of the purifying-refrigerating column through a conduit 20, 21, 22 passing through the said exchange system, so as to supply the said column 1 with a subcooled liquid distillate.

* * * * *